United States Patent [19]

Hudson, III et al.

[11] Patent Number: 4,989,836
[45] Date of Patent: Feb. 5, 1991

[54] DETACHABLE WHEELCHAIR HEADREST

[75] Inventors: E. W. Hudson, III, Tempe; Lewis B. Anderson, Glendale, both of Ariz.

[73] Assignee: Premier Solutions, Ltd., Tempe, Ariz.

[21] Appl. No.: 333,175

[22] Filed: Apr. 4, 1989

[51] Int. Cl.$^5$ .................................. A47C 1/10
[52] U.S. Cl. ........................... 297/391; 297/DIG. 4; 297/464
[58] Field of Search ............... 297/391, 396, DIG. 4, 297/441, 464, DIG. 6, 444, 218

[56] References Cited

U.S. PATENT DOCUMENTS

| 3,101,973 | 8/1963 | Toth | 297/391 |
| 3,186,759 | 6/1965 | Reeves . | |
| 3,497,259 | 2/1970 | Sherfey . | |
| 3,512,834 | 5/1970 | Lockshin | 297/441 |
| 3,596,655 | 8/1971 | Corcoran | 297/391 |
| 3,632,162 | 1/1972 | Trethaway . | |
| 3,674,310 | 7/1972 | Montagano . | |
| 3,730,589 | 5/1973 | Lane . | |
| 4,030,781 | 6/1977 | Howard . | |
| 4,085,946 | 4/1978 | Krupp . | |
| 4,101,143 | 7/1978 | Sieber | 297/DIG. 4 |
| 4,415,177 | 11/1983 | Hale et al. . | |
| 4,498,704 | 2/1985 | Hildreth . | |
| 4,565,385 | 1/1986 | Morford | 297/DIG. 4 |
| 4,592,570 | 6/1986 | Nassiri | 297/DIG. 4 |
| 4,655,471 | 4/1987 | Peek . | |
| 4,746,168 | 5/1988 | Bracesco | 297/88 X |
| 4,789,201 | 12/1988 | Selbert | 297/218 |
| 4,838,611 | 6/1989 | Talaugon | 297/391 |

FOREIGN PATENT DOCUMENTS

| 2708398 | 8/1978 | Fed. Rep. of Germany . |
| 2856366 | 2/1980 | Fed. Rep. of Germany ... 297/DIG. 6 |
| 2938879 | 4/1981 | Fed. Rep. of Germany . |

OTHER PUBLICATIONS

Safety Travel Chairs, Inc., 9-1981.

Primary Examiner—Peter A. Aschenbrenner
Attorney, Agent, or Firm—Cahill, Sutton & Thomas

[57] ABSTRACT

A wheelchair headrest, attached to opposite vertical frame members of the wheelchair, includes at least two resilient head supports for preventing involuntary head movement in a person seated in the wheelchair. The wheelchair headrest is detachable from the wheelchair and can be easily folded for transport or storage. A padded band attached to the head supports passes around the person's forehead preventing involuntary forward head tilting.

10 Claims, 2 Drawing Sheets

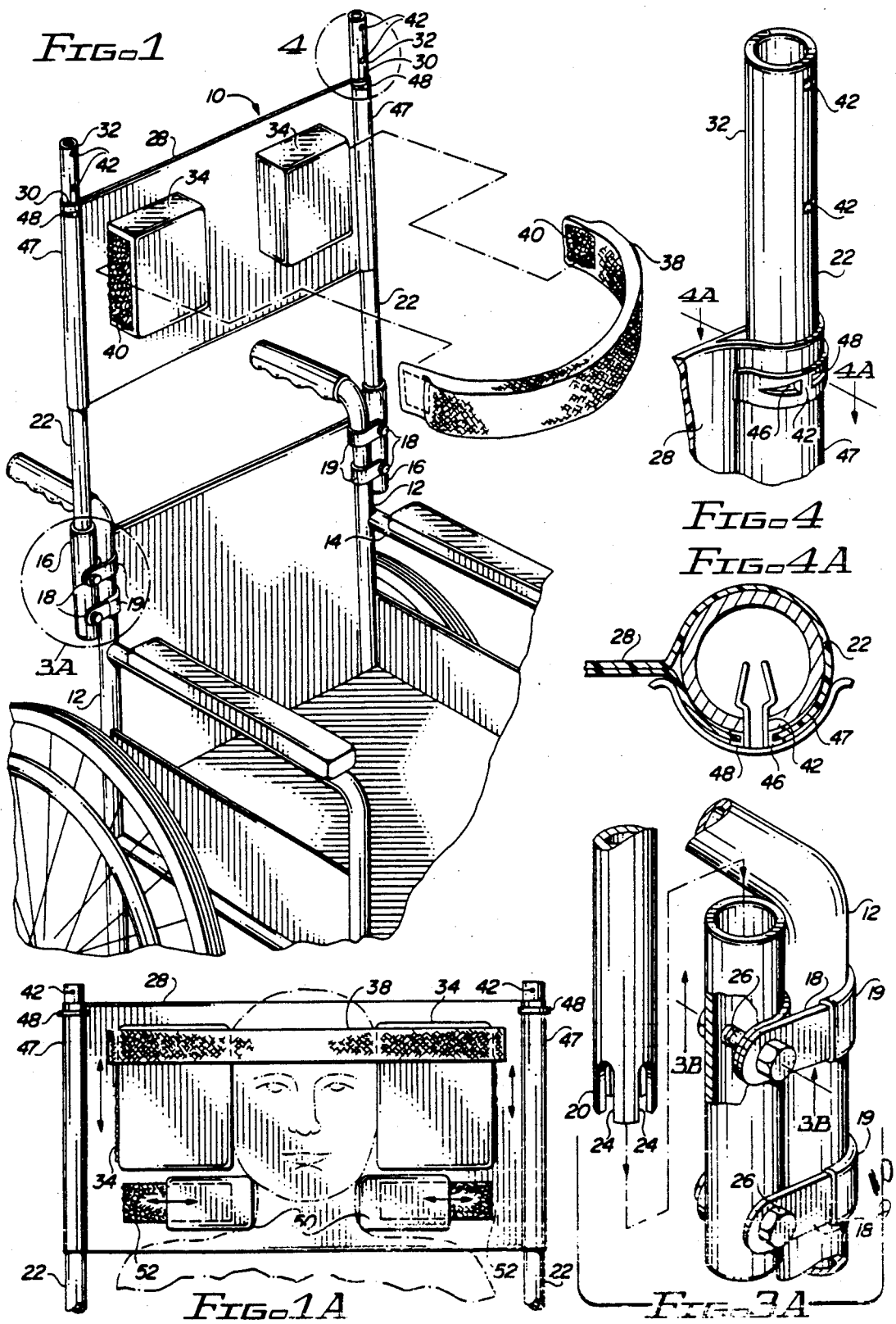

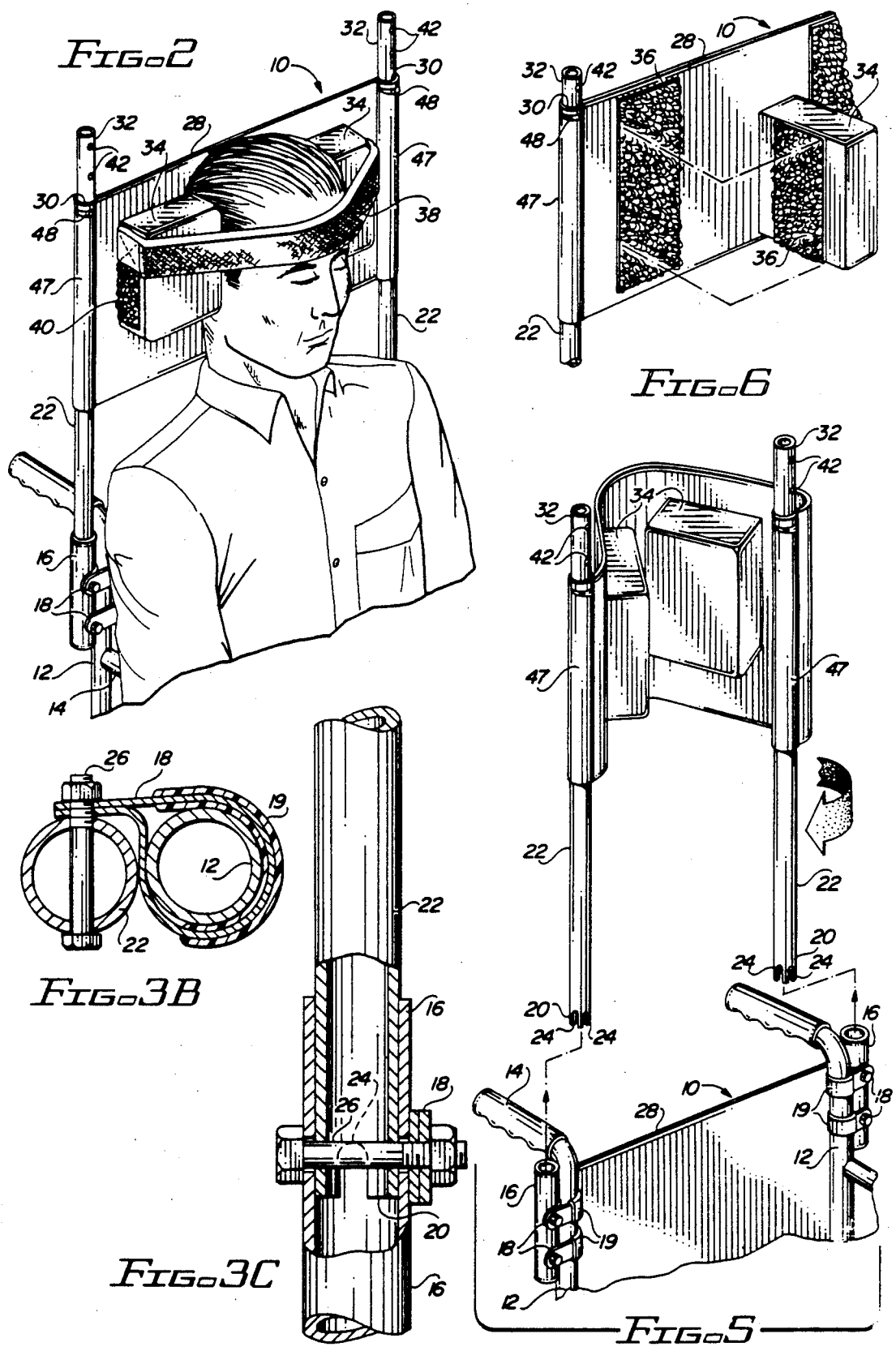

DETACHABLE WHEELCHAIR HEADREST

BACKGROUND OF THE INVENTION

The invention relates to a detachable wheelchair headrest for preventing involuntary head movement in persons seated in the wheelchair.

Many infirm, paralyzed, or elderly persons have inadequate use or control of their neck muscles. When such persons are seated in a wheelchair, their weak neck muscles often allow their head to wobble uncontrollably forward and from side-to-side.

The prior art discloses a number of detachable wheelchair headrests made from flexible materials. See for example U.S. Pat. No. 4,498,704 (Hildreth), U.S. Pat. No. 4,415,177 (Hale et al.), U.S. Pat. No. 4,030,781 (Howard, disclosing a pillow headrest for a lawnchair), U.S. Pat. No. 3,674,310 (Montagno), U.S. Pat. No. 3,632,162 (Trethawny), U.S. Pat. No. 3,497,259 (Sherfey), and U.S. Pat. No. 3,186,759 (Reeves). However, without exception, these prior art headrests merely provide a comfortable surface on which to rest the head of a person sitting in a wheelchair, without providing any means for restraining or preventing involuntary head movement. Furthermore, most of the headrests do not fold easily for transport or storage.

U.S. Pat. No. 3,703,589 (Lane) discloses a detachable wheelchair headrest with inclined head supports for cradling the head of a person seated in the wheelchair. The Lane headrest does not effectively reduce side-to-side head wobble, and involuntary forward head motion is not restrained.

Thus, there is an unmet need for a wheelchair headrest which can prevent involuntary head movement in persons seated in the wheelchair, and which can be easily detached from the wheelchair and folded for convenient transport or storage.

SUMMARY OF THE INVENTION

Accordingly, it is an object of the invention to provide a wheelchair headrest for preventing involuntary head movement in persons seated in the wheelchair.

It is another object of the invention to provide a wheelchair headrest which can be quickly and easily attached to many different types of wheelchairs.

It is another object of the invention to provide a wheelchair headrest which can be conveniently detached from the wheelchair and folded compactly for efficient transport or storage.

It is another object of the invention to provide a wheelchair headrest which can be easily and inexpensively manufactured from standard components.

Briefly described, and in accordance with one embodiment, the invention provides a wheelchair headrest attached to opposite vertical frame members of the wheelchair, for preventing involuntary head movement in a person seated in the wheelchair. Each of a pair of upright mounting tubes is attached to the outside of one of the wheelchair vertical frame members. The lower ends of a pair of upright headrest poles are detachably retained in the mounting tubes. The upper ends of the headrest poles are received in lengthwise tubular openings located on opposite side edges of a flexible panel. At least two resilient head supports are attached to the front face of the panel and spaced for receiving therebetween the head of a person seated in the wheelchair, thereby restraining the head from involuntary side-to-side wobbling. An optional padded strap having ends attached to the head supports passes around the person's forehead to prevent involuntary forward tilting of the person's head.

BRIEF DESCRIPTION OF THE DRAWINGS

FIG. 1 is a perspective view of one embodiment of the wheelchair headrest of the present invention.

FIG. 1A is a partial elevational view of a person whose head and neck are situated between head and neck supports attached to a panel of the wheelchair headrest.

FIG. 2 is a perspective view of a person's head restrained by the headrest of FIG. 1.

FIG. 3A is a partial perspective view of a headrest mounting tube attached to a wheelchair vertical frame member by a screw clamp, and a headrest pole having a notched lower end for insertion in the mounting tube and retention by the screw of the screw clamp.

FIG. 3B is a sectional view taken on line 3B—3B of FIG. 3A.

FIG. 3C is a partial cut-away cross-sectional view of a headrest pole inserted into a mounting tube.

FIG. 4 is a partial perspective view showing a clip inserted through aligned panel side edge and headrest pole holes.

FIG. 4A is a closeup cross-sectional view taken on line 4A—4A of FIG. 4.

FIG. 5 is a perspective view showing removal of the headrest of FIG. 1 from the wheelchair and folding for transport or storage.

FIG. 6 is a partial perspective view of a detachable headrest head support.

DETAILED DESCRIPTION OF THE PREFERRED EMBODIMENTS

FIGS. 1 and 2 illustrate a wheelchair headrest 10 attached to opposite vertical frame members 12 of a wheelchair 14. Wheelchair headrest 10 includes a pair of upright mounting tubes 16, each of which is secured to the outside of one of vertical frame members 12 by means of screw clamps 18, illustrated in greater detail in FIGS. 3A-3C. Preferably, screw clamps 18 include neoprene-coated sections 19 to provide increased adhesion to vertical frame member 12, thereby preventing slippage of the screw clamps. Preferably, the neoprene-coated sections 19 wrap almost entirely around frame members 12, as shown in FIG. 3B.

Headrest poles 22 are inserted in mounting tubes 16. As illustrated in FIGS. 3A and 3C, headrest poles 22 can be detachably retained in mounting tubes 16 by providing lower ends 20 of headrest pole with at least one pair, and preferably, two pairs of oppositely spaced notches 24 for engagement with screws 26 when the headrest poles are inserted in the mounting tubes. Headrest poles 22 can be removed from mounting tubes 16 by lifting the headrest poles up off the screws 26. Mounting tubes 16 and headrest poles 22 preferably are made of suitable metal or reinforced plastic tubing.

Wheelchair headrest 10 further includes panel 28, made of a flexible material such as vinyl or canvas. Panel 28 has lengthwise tubular sleeves 30 on opposite side edges 47 thereof for detachably receiving upper ends 32 of headrest poles 22. At least two head supports 34 are attached to the front face of panel 28, preferably by detachable means such as velcro fastenings 36 (illustrated in FIG. 6) or snap fastenings (not shown), so that when headrest 10 is detached from wheelchair 14, the headrest can be conveniently folded, or rolled up around headrest poles 22.

As illustrated in FIG. 2, head supports 34 are spaced on panel 28 at a distance suitable for receiving therebetween the head of a person seated in wheelchair 14, thereby restraining the head from the involuntary side-to-side wobbling caused by weak neck muscles. Preferably, head supports 34 are made from a comfortably resilient yet supportive material such as foam rubber. In addition, head supports 34 may be encased in the same flexible material from which panel 28 is constructed.

To prevent involuntary forward head movement, the person's forehead can be restrained by flexible head band 38, removably attached to the sides of head supports 34, preferably by velcro fasteners 40. Attachment of head band 38 in the manner shown by velcro fasteners 40 ensures that the head band 40 does not slip downward over the person's face and under his or her chin, and thereby avoids any risk of choking the person. Alternatively, flexible head band 38 can be attached to head supports 34 by means of snap fasteners. FIG. 2 clearly illustrates how head band 38 can comfortably restrain a person's head from involuntary forward movement As illustrated most clearly in FIGS. 4 and 4A, headrest poles 22 are aligned with eyelets 46 located on each opposite side edge 47 of panel 28 so that when the headrest poles are inserted into panel edge sleeves 30, the side edge eyelets 46 are aligned with the headrest pole holes 42. Clip or snap fastener 48 is inserted into the aligned side edge eyelets 46 and headrest pole holes 42 to prevent panel 28 from slipping down headrest poles 22, thereby securely supporting the panel 28 in position on the headrest poles. Several holes such as 42 are vertically spaced on headrest poles 22 to allow the vertical position of panel 28 to be adjusted relative to the height of the person seated in wheelchair 14.

Panel 28 may stretch during use, causing an undesirable slackness in panel 28 and a corresponding loss in effective head restraint. Because panel 28 is maintained in position on headrest poles 22 either by means of clip 48 cr by means of snap fasteners, turning at least one headrest pole as described above has the effect of tightening the panel between the headrest poles. The slackness, or tension, of panel 28 can be adjusted by lifting and turning at least one headrest pole 22 a quarter of a turn so as to tighten or loosen panel 28 until screw 26 engages another pair of oppositely positioned notches 24. More precise adjustments in the tension of panel 28 can be made by including additional pairs of oppositely-spaced notches on lower ends 20 of poles 22.

As illustrated in Fig. 1A, wheelchair headrest 10 also may include at least two resilient neck supports 50 attached to the front face of panel 28 beneath head supports 34 by velcro fastenings 52 or, alternatively, snap fasteners. Neck supports 50 are spaced for receiving therebetween the neck of a person seated in wheelchair 14, thereby providing additional support for weak neck muscles and restraint of the neck from involuntary movement.

As shown in FIG. 5, headrest 10 can be easily removed from wheelchair 14 by lifting headrest poles 22 out of mounting tubes 16. Headrest 10 can then be easily moved or folded for storage. Or, as illustrated in FIG. 6, head supports 34 can be removed, so that panel 28 can be conveniently rolled into a small tubular configuration with headrest poles 22.

The above described headrest thus achieves effective control of side-to-side wobble and forward tilt of a patient's head without discomfort. The headrest is easily attachable to and removable from most wheelchairs, allowing the headrest to be removed and folded and stored while the patient is being wheeled about, and can be quickly attached and adjusted if the patient is left alone for a while in the wheelchair.

While the invention has been described with reference to several particular embodiments thereof, those skilled in the art will be able to make the various modifications to the described embodiments of the invention without departing from the true spirit and scope of the invention. For example, headrest poles 22 can be attached to mounting tubes 16 by fixing the headrest poles to the mounting tubes with screws or other easily detachable fastener. Alternatively, panel 28 can be maintained in position on headrest poles 22 by means of panel snaps and corresponding headrest pole snap fasteners.

We claim:

1. A headrest attached to first and second vertical frame members of a wheelchair, for preventing involuntary head movement by a person seated in the wheelchair, the headrest comprising in combination:
    (a) upright first and second mounting tubes attached to the first and second vertical frame members, respectively;
    (b) upright first and second headrest poles each having a lower end inserted in the first and second mounting tubes, respectively;
    (c) a flexible panel having parallel first and second sleeves attached to opposed first and second side edges thereof, the first and second headrest poles extending through the first and second sleeves, respectively; and
    (d) first and second resilient head supports attached to a front face of the panel and spaced apart to restrain the head from involuntary side-to-side wobbling, wherein each of the first and second headrest poles has in its lower end a first pair of opposed notches, and wherein each of the first and second headrest poles has in its lower end a second pair of opposed notches, the first and second mounting tubes having therein means for engaging the notches of the first and second headrest poles, respectively, so that tension of the flexible panel can be more precisely adjusted by turning one of the first and second headrest poles to engage the second pair of notches.

2. The headrest of claim 1 further comprising means for attaching said first and second sleeves to said first and second headrest poles, respectively.

3. The headrest of claim 2 wherein the attaching means comprises first and second eyelets in the first and second sleeves, respectively, aligned with first and second holes in said first and second headrest poles, respectively, and a first snap fastener extending through the first eyelet and the first hole, and a second snap fastener extending through the second eyelet and the second hole.

4. The headrest of claim 3 further comprising a flexible band attached to the first and second head supports and extending around the person's forehead to prevent forward tilting of the head.

5. The headrest of claim 4 including velcro attachment means for attaching first and second ends of the band to the first and second head supports, respectively.

6. The headrest of claim 1 wherein the flexible panel is composed of vinyl.

7. A headrest attached to first and second vertical frame members of a wheelchair, for preventing involuntary head movement by a person seated in the wheelchair, the headrest comprising in combination:
   (a) upright first and second poles connected to the first and second vertical frame members, respectively;
   (b) a flexible panel having parallel first and second sleeves attached to opposed first and second side edges thereof, the first and second poles extending through the first and second sleeves, respectively;
   (c) a first and second head supports attached to a front face of the panel and spaced apart to restrain the head from involuntary side-to-side wobbling, and
   (d) first and second means for connecting the first and second poles to the first and second vertical frame members, respectively, the first connecting means including means for allowing rotation of the first pole to adjust tension of the flexible panel and means for locking the first pole into fixed non-rotational relationship to the first vertical frame member to maintain the tension of the flexible panel.

8. A method for preventing involuntary head movement in a person seated in a chair having first and second vertical frame members, comprising the steps of:
   (a) attaching upright first and second poles to the first and second vertical frame members, respectively;
   (b) inserting the first and second poles into parallel first and second sleeves attached to opposed first and second side edges of a flexible panel;
   (c) attaching to a front face of the panel first and second head supports spaced apart;
   (d) positioning the head between the first and second head supports;
   (e) restraining sideways movement of the head by means of the first and second head supports, and
   (f) adjusting tension of the flexible panel by rotating the first pole and then locking that pole into fixed, non-rotational relationship with the first vertical frame member.

9. The method of claim 8 further comprising the steps of:
   (a) attaching a flexible head band to the first and second head supports;
   (b) placing the flexible head band around the person's forehead; and
   (c) restraining forward movement of the head by means of the flexible head band.

10. The headrest of claim 7 wherein the first and second connecting means include means for effectuating quick removal of the headrest from the wheelchair by simply urging the first and second poles upward.

* * * * *